(12) United States Patent
Akinay et al.

(10) Patent No.: US 12,193,929 B2
(45) Date of Patent: Jan. 14, 2025

(54) IN-SITU ADJUSTABLE INTRAOCULAR LENS

(71) Applicant: Alcon Inc., Fribourg (CH)

(72) Inventors: Ali Akinay, Southlake, TX (US); Xuwei Jiang, Arlington, TX (US); Jian Liu, Keller, TX (US); Jingbo Liu, Keller, TX (US)

(73) Assignee: Alcon Inc., Fribourg (CH)

( * ) Notice: Subject to any disclaimer, the term of this patent is extended or adjusted under 35 U.S.C. 154(b) by 0 days.

(21) Appl. No.: 18/325,280

(22) Filed: May 30, 2023

(65) Prior Publication Data

US 2023/0320841 A1 Oct. 12, 2023

Related U.S. Application Data

(62) Division of application No. 16/840,660, filed on Apr. 6, 2020, now Pat. No. 11,701,220.

(60) Provisional application No. 62/831,520, filed on Apr. 9, 2019.

(51) Int. Cl.
| | |
|---|---|
| *A61F 2/16* | (2006.01) |
| *A61F 9/008* | (2006.01) |
| *A61L 27/16* | (2006.01) |
| *A61L 27/26* | (2006.01) |
| *A61L 27/50* | (2006.01) |

(52) U.S. Cl.
CPC ............... *A61F 2/16* (2013.01); *A61F 9/008* (2013.01); *A61L 27/16* (2013.01); *A61L 27/26* (2013.01); *A61L 27/50* (2013.01); *A61F 2/1629* (2013.01); *A61F 2/1632* (2013.01); *A61F 2002/1686* (2013.01); *A61F 2002/1689* (2013.01); *A61F 2002/16901* (2015.04); *A61L 2430/16* (2013.01)

(58) Field of Classification Search
CPC ...... A61F 2/1629; A61F 2/1632; A61F 9/008; A61L 27/50
See application file for complete search history.

(56) References Cited

U.S. PATENT DOCUMENTS

| | | | |
|---|---|---|---|
| 5,728,155 A * | 3/1998 | Anello ................. | A61F 2/1629 623/6.47 |
| 2007/0010881 A1* | 1/2007 | Soye ..................... | A61F 2/1694 623/6.22 |

(Continued)

FOREIGN PATENT DOCUMENTS

| | | |
|---|---|---|
| JP | 2006517447 A | 7/2006 |
| JP | 2007262195 A | 10/2007 |

(Continued)

OTHER PUBLICATIONS

Ikeda Tomiki et al., "Photic driving polymer liquid crystal film-plastic that bends freely with light", Applied physics, Jul. 10, 2004, 73, 7, pp. 947-951, Abstract translation.

*Primary Examiner* — Javier G Blanco

(57) ABSTRACT

The present disclosure provides an intralocular-lens (IOL) or ophthalmic device including an optic and at least one haptic, at least a portion of which is formed from a photoresponsive shape memory polymer network, such as a polydomain azo liquid crystalline polymer network (PD-LCN). The present disclosure further provides systems and methods for adjusting the position of such an IOL or other ophthalmic device using polarized laser radiation.

4 Claims, 8 Drawing Sheets

(56) References Cited

U.S. PATENT DOCUMENTS

| | | | |
|---|---|---|---|
| 2007/0299487 A1* | 12/2007 | Shadduck | A61F 2/145 623/6.56 |
| 2010/0082017 A1* | 4/2010 | Zickler | A61F 2/1624 606/4 |
| 2014/0094908 A1* | 4/2014 | Zaldivar | A61F 2/1618 623/6.12 |
| 2018/0085213 A1* | 3/2018 | Hadba | A61F 2/1618 |
| 2019/0053890 A1* | 2/2019 | Chien | C07C 69/54 |

FOREIGN PATENT DOCUMENTS

| | | | | |
|---|---|---|---|---|
| JP | 2008019744 A | 1/2008 | | |
| JP | 2013245296 A | 12/2013 | | |
| WO | 2004072689 A2 | 8/2004 | | |
| WO | WO-2010125596 A1 * | 11/2010 | | A61F 2/1613 |

* cited by examiner

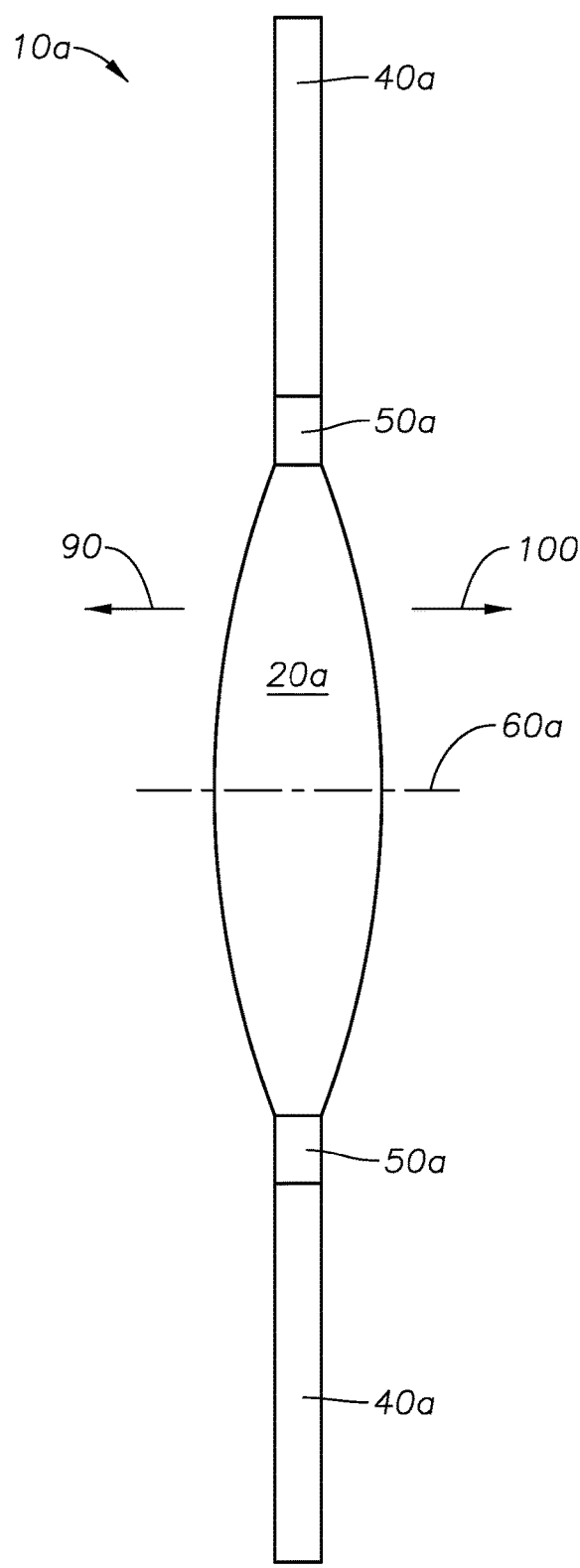
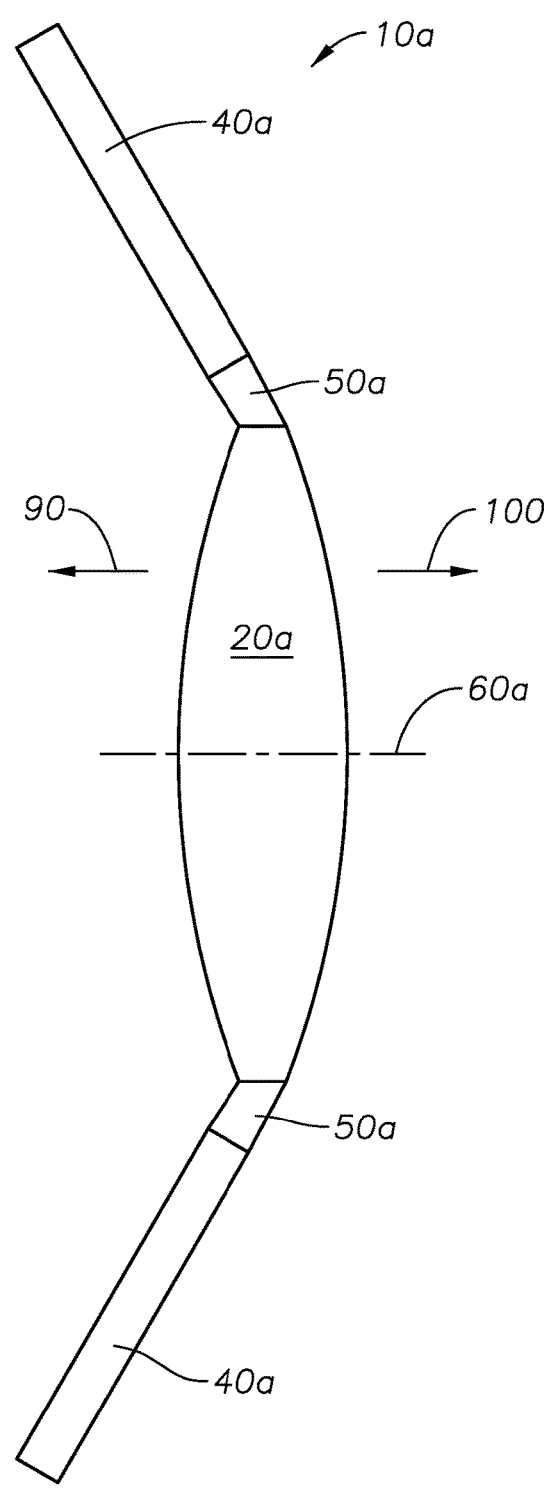
FIG. 1B
FIG. 1C

IN-SITU ADJUSTABLE INTRAOCULAR LENS

PRIORITY CLAIM

This application claims the benefit of priority of U.S. Provisional Patent Application Ser. No. 62/831,520 titled "IN-SITU ADJUSTABLE INTRAOCULAR LENS," filed on Apr. 9, 2019, whose inventors are Xuwei Jiang, Ali Akinay, Jingbo Liu, and Jian Liu, which is hereby incorporated by reference in its entirety as though fully and completely set forth herein.

TECHNICAL FIELD

The present disclosure relates to an intraocular lens (IOL) for which the position may be adjusted in-situ in the capsular bag of the eye. The present disclosure further relates to methods of adjusting the position of such an IOL and a system for adjusting the IOL position.

BACKGROUND

The human eye includes a cornea and a crystalline lens that are intended to focus light that enters the pupil of the eye onto the retina. However, the eye may exhibit various refractive errors, which result in light not being properly focused upon the retina, and which may reduce visual acuity. Many interventions have been developed over the years to correct various ocular aberrations. These include spectacles, contact lenses, corneal refractive surgery, such as laser-assisted in situ keratomileusis (LASIK) or corneal implants, and IOLs. IOLs are also used to treat cataracts by replacing the natural diseased crystalline lens of the eye of a patient. During typical IOL-placement surgery, an IOL is inserted into the capsular bag of a patient to replace the natural crystalline lens.

Whether implanted for refractive errors or for cataract treatment, an IOL may not always be located in the predicted position after surgery. In addition, the IOL may potentially shift, either rotationally or axially or in combination, within the capsular bag over time, so that it is no longer in the predicted position. An improperly positioned IOL may negatively impact the patient's quality of vision, as the location of the IOL in the eye impacts refractive power and, in applicable cases, astigmatic correction. Therefore, a predicted position of the IOL in the eye is used to develop a surgical plan and select a particular IOL for a patient. When the actual position of the IOL deviates from the predicted position in the surgical plan, the outcome may be suboptimal.

SUMMARY

The present disclosure provides an intralocular-lens (IOL) including an optic and at least one haptic, at least a portion of which is formed from a polydomain azo liquid crystalline polymer network (PD-LCN).

In further details, which may be combined with one another or with any other portions of this disclosure in any combinations, unless clearly mutually exclusive, the disclosure further provides:
  i) the at least one haptic may include a haptic junction, at least a portion of which is formed from PD-LCN;
  ii) the at least one haptic may be attached to the optic via the haptic junction;
iv) the IOL may further include a base which holds the optic and the at least one haptic may be attached to the base;
  v) the IOL may include a plurality of haptics and at least a portion of each may be formed from PD-LCN;
  vi) each haptic may include a haptic junction, at least a portion of which may be formed from PD-LCN;
  vii) the PD-LCN may include crosslinked diacrylate liquid crystal monomer and diacrylate azobezene liquid crystal monomer;
  viii) the PD-LCN may include 25 wt % or less diacrylate azobenzene liquid crystal monomer;
  ix) the PD-LCN may have a crosslink density of between 1.0 mol/dm$^3$ and 8.0 mol/dm$^3$;
  x) the diacrylate liquid crystal monomer may include 4-(3-Acryloyloxypropyloxy)-benzoesure 2-methyl-1,4-phenylester;
  xi) the diacrylate azobezene liquid crystal monomer may include 4,4'-bis[6-acryloloxy) hexyloxy] azobenzene;
  xii) the diacrylate liquid crystal monomer may include 4-(3-Acryloyloxypropyloxy)-benzoesure 2-methyl-1,4-phenylester and the diacrylate azobezene liquid crystal monomer may include 4,4'-bis[6-acryloloxy) hexyloxy] azobenzene.

The present disclosure further provides an ophthalmic device including a base including an opening configured to receive an optic of an intra-ocular lens and at least one haptic coupled to the base, at least a portion of the at least one haptic comprising a photoresponsive shape memory polymer network.

In further details, which may be combined with one another or with any other portions of this disclosure in any combinations, unless clearly mutually exclusive, the disclosure further provides:
  i) the photoresponsive shape memory polymer network may include a polydomain azo liquid crystalline polymer network (PD-LCN);
  ii) the at least one haptic may include a haptic junction, at least a portion of which may be formed from the photoresponsive shape memory polymer network;
  iii) the at least one haptic may be attached to the optic via the haptic junction;
  iv) the at least one haptic may include a plurality of haptics and at least a portion of each may be formed from the photoresponsive shape memory polymer network;
  v) the PD-LCN may include crosslinked diacrylate liquid crystal monomer and diacrylate azobezene liquid crystal monomer;
  vi) the PD-LCN may include 25 wt % or less diacrylate azobenzene liquid crystal monomer;
  vii) the PD-LCN may have a crosslink density of between 1.0 mol/dm$^3$ and 8.0 mol/dm$^3$.
  viii) the diacrylate liquid crystal monomer may include 4-(3-Acryloyloxypropyloxy)-benzoesure 2-methyl-1,4-phenylester;
  ix) the diacrylate azobezene liquid crystal monomer may include 4,4'-bis[6-acryloloxy)hexyloxy]azobenzene;
  x) the diacrylate liquid crystal monomer may include 4-(3-Acryloyloxypropyloxy)-benzoesure 2-methyl-1,4-phenylester and the diacrylate azobezene liquid crystal monomer comprises 4,4'-bis[6-acryloloxy) hexyloxy] azobenzene.

The present disclosure may include a method of adjusting an IOL or an ophthalmic device. The IOL or ophthalmic device may be any IOL or ophthalmic device described above or elsewhere in this disclosure. The method may include irradiating a portion of a haptic of the IOL or ophthalmic device, in which the haptic includes a photoresponsive shape memory polymer network, such as PD-LCN, with polarized laser radiation to cause the photoresponsive shape memory polymer network, such as PD-LCN, to bend to a bending angle, thereby pushing against a capsular bag in which the IOL or ophthalmic device is located and adjusting the position of the IOL or ophthalmic device in the capsular bag.

In further details, which may be combined with one another or with any other portions of this disclosure in any combinations, unless clearly mutually exclusive, the disclosure further provides:

i) the polarized laser radiation may have a wavelength in the range of 440 nm to 514 nm, including the endpoints;
ii) the position of the IOL may be adjusted axially forward or backward;
iii) the position of the IOL may be adjusted radially by an angle;
iv) the IOL may be in an actual position in the capsular bag that is different from a target position, and adjusting the position of the IOL may include moving the IOL to the target position;
v) irradiating may occurs for from between 0.5 seconds and 5 minutes, including the endpoints.

The present disclosure provides a method of correcting refractive error. The method includes implanting, in the eye of a patient, an IOL or ophthalmic device including at least one haptic, at least a portion of the at least one haptic including a photoresponsive shape memory polymer network, obtaining post-surgical biometric data for the eye of the patient, determining a post-surgical refractive error of the eye of the patient, based on the post-surgical biometric data and post-surgical refractive error, generating a nomogram to control a laser to apply polarized laser radiation to the photoresponsive shape memory polymer network to induce a shape change of the haptics and thereby cause the intraocular lens to at least one of translate or rotate in the eye of the patient, thereby correcting the post-surgical refractive error, and irradiating the photoresponsive shape memory polymer network using the laser. The IOL or ophthalmic device may be any IOL or ophthalmic device described above or elsewhere in this disclosure.

In further details, which may be combined with one another or with any other portions of this disclosure in any combinations, unless clearly mutually exclusive, the disclosure further provides:

i) the photoresponsive shape memory polymer network comprises a PD-LCN;
ii) the polarized laser radiation may have a wavelength in the range of 440 nm to 514 nm, including the endpoints;
iii) the position of the IOL may be adjusted axially posteriorly or anteriorly;
iv) the position of the IOL may be adjusted radially by an angle θ;
v) irradiating may occur for from between 0.5 seconds and 5 minutes, including the endpoints;
vi) the irradiated portion of the haptic comprising the PD-LCN may include a haptic junction.

The present disclosure further provides a surgical system for adjusting the position of an IOL or ophthalmic device, such as any IOL or ophthalmic device described above or elsewhere in this disclosure. The system includes a laser able to provide laser radiation in the range of 440 nm to 514 nm, including the endpoints, a polarization filter able to adjust the angle or polarization of radiation from the laser, and a computer comprising a processor, a memory, and a communications interface, in which the computer is able to execute, using the processor, instructions stored in the memory to cause instructions to be sent through the communications interface to cause the laser and the polarization filter to irradiate at least a portion of a haptic of an IOL or ophthalmic device located in the capsular bag of an eye of a patient with polarized laser radiation, wherein the irradiated portion includes a photoresponsive shape memory polymer network comprises, such as a PD-LCN, and bends to a bending angle in response to the radiation. The instructions may include all or part of any method described above or otherwise disclosed herein.

In further details, which may be combined with one another or with any other portions of this disclosure in any combinations, unless clearly mutually exclusive, the disclosure further provides:

i) the irradiated portion of the haptic includes a haptic junction;
ii) the laser may include a femtosecond laser or an excimer laser.

BRIEF DESCRIPTION OF THE DRAWINGS

For a more complete understanding of the present disclosure, reference is now made to the following description, taken in conjunction with the accompanying drawings illustrating aspects of the present disclosure, in which like components have like numerals, including with alphabetic designations of variants, such as 10a, 10b, and in which:

FIG. 1B is a schematic side-view diagram of the single-piece IOL of FIG. 1A;

FIG. 1C is a schematic side-view diagram of the single-piece IOL of FIG. 1A and FIG. 1B with the PD-LNC bent to approximately a 40° bending angle.

DETAILED DESCRIPTION

The present disclosure relates to an intraocular lens (IOL) for which the position may be adjusted in-situ. The present disclosure further relates to methods of adjusting the position of such an IOL and a system for adjusting the IOL position. In particular, an IOL of the present disclosure may include at least one haptic, at least a portion of which is formed from a photoresponsive shape memory polymer network, such as a polydomain azo liquid crystalline polymer network (PD-LCN). The PD-LCN will predictably bend in a given direction in response to a particular wavelength of laser radiation with a particular polarization, allowing adjustments to the IOL position within the eye. In addition, the PD-LCN will retain its shape so that the adjusted IOL position is retained. Further, PD-LCN bending and thus IOL position adjustment is reversible in response to a different polarization of the laser radiation.

An IOL of the present disclosure may be a single-piece or modular IOL (e.g., a two-piece or three-piece IOL). In general, an IOL includes at least one optic and at least one haptic. The haptic is located on the side(s) of the optic and helps maintain the IOL in a stable position within the eye. Depending on the IOL design, the haptic may be integrated with or directly coupled to the optic. In some designs, the IOL may also include a separate or integral base with which the optic and/or haptics may be integrated or coupled. The base may hold the optic, and the haptic may be attached to the base. The region of the haptic that attaches to the optic or the base is referred to herein as the haptic junction. Components of a modular IOL may be individually inserted and assembled within the eye during surgery.

The entire haptic, a portion thereof, or only the haptic junction may be formed from PD-LCN. Some IOLs of the present disclosure may include a plurality of haptics. In such a case, all of the haptics may include at least a portion formed from PD-LCN. For example, all of the haptics may have a haptic junction formed from PD-LCN. In some IOLs with a plurality of haptics, symmetrically placed haptics, such as haptics opposite one another or haptics at 120 degree angles may have the same placements of PD-LCN, to allow symmetrical adjustment of IOL position. In addition, in some IOLs with a plurality of haptics, set of haptics, particularly sets whose members are symmetrically placed, may have different placements of PD-LCN to allow the haptics to respond differently to polarized laser radiation, allowing more fine-tuned adjustment of IOL position.

All IOLs occasionally experience improper placement, so the present disclosure is compatible with any type of IOL. Specific IOLs are described in FIGS. 1-7 to demonstrate how PD-LCN may be used in IOLs. One of ordinary skill in the art, with the benefit of the present disclosure, may determine an appropriate placement of PD-LCN in many other types of IOLs in addition to those specifically illustrated.

Figure 1A:
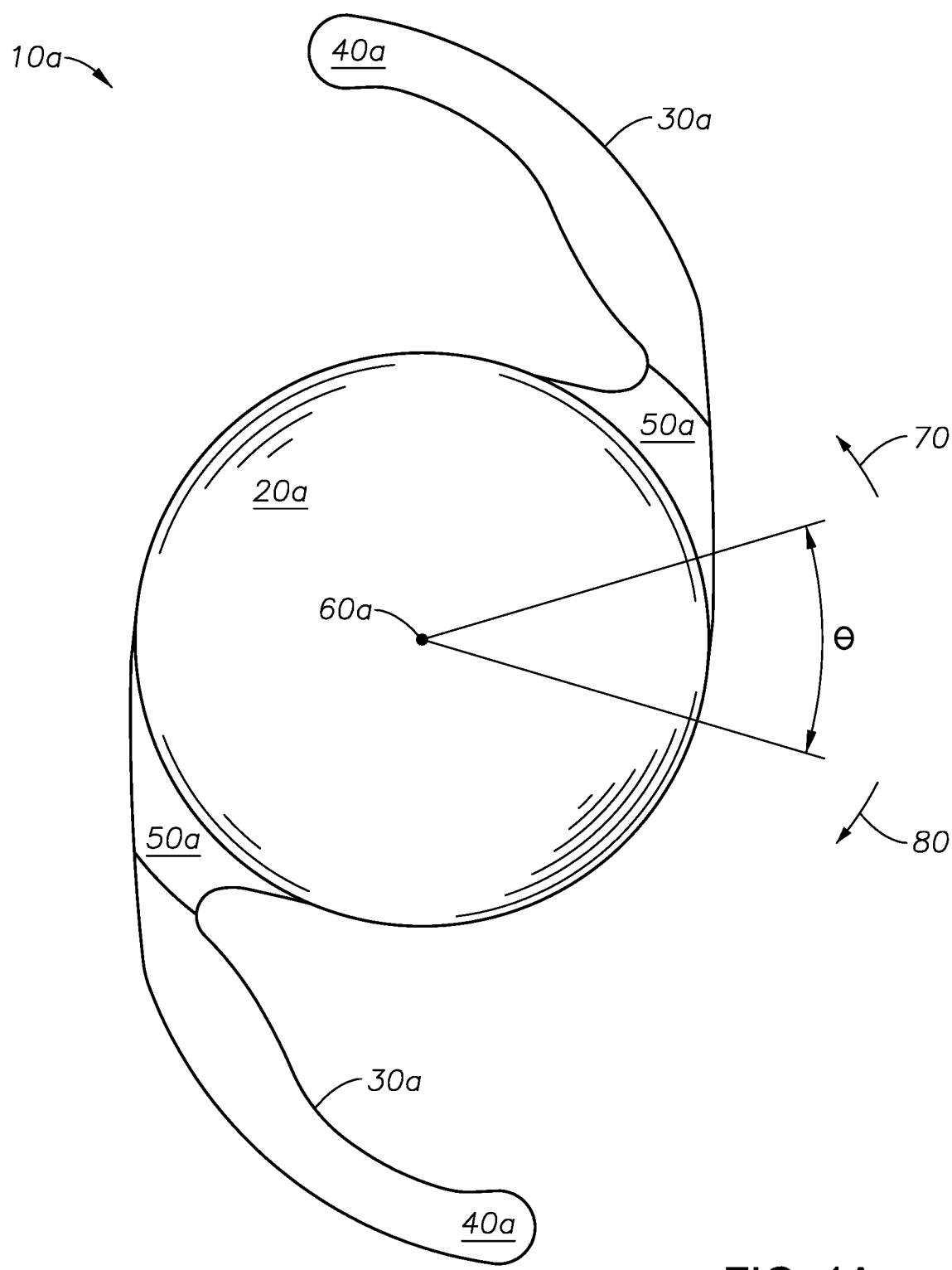
FIG. 1A is a schematic top view diagram of a single-piece IOL having two haptics.

FIG. 1A is a schematic diagram of an IOL $10a$ including an optic $20a$ and two haptics $30a$ attached to the optic $20a$ and/or a base (not shown). Each of the haptics $30a$ has an arm $40a$ and a haptic junction $50a$ between the arm $40a$ and the optic $20a$. The haptic junction $50a$ may attach the haptic $30a$ to the optic $20a$ (or base). The IOL also has a center $60a$. Once it is implanted and secure in the capsular bag, the IOL $10a$ may be rotated around the center $60a$ in a direction 70 or a direction 80 by an angle θ by irradiating one or more of the haptic junctions $50a$ to cause the PD-LNC to change shape. As illustrated in FIG. 1B, the IOL $10a$ may also move forward (anteriorly) in the eye in direction 90 or backward (posteriorly) in the eye direction 100. FIG. 1C shows the IOL $10a$, after both haptic junctions $50a$ have been irradiated to cause the PD-LNC to bend to approximately a 40° bending angle, pushing the IOL backward (posteriorly) in the eye in direction 100.

Figure 2A:
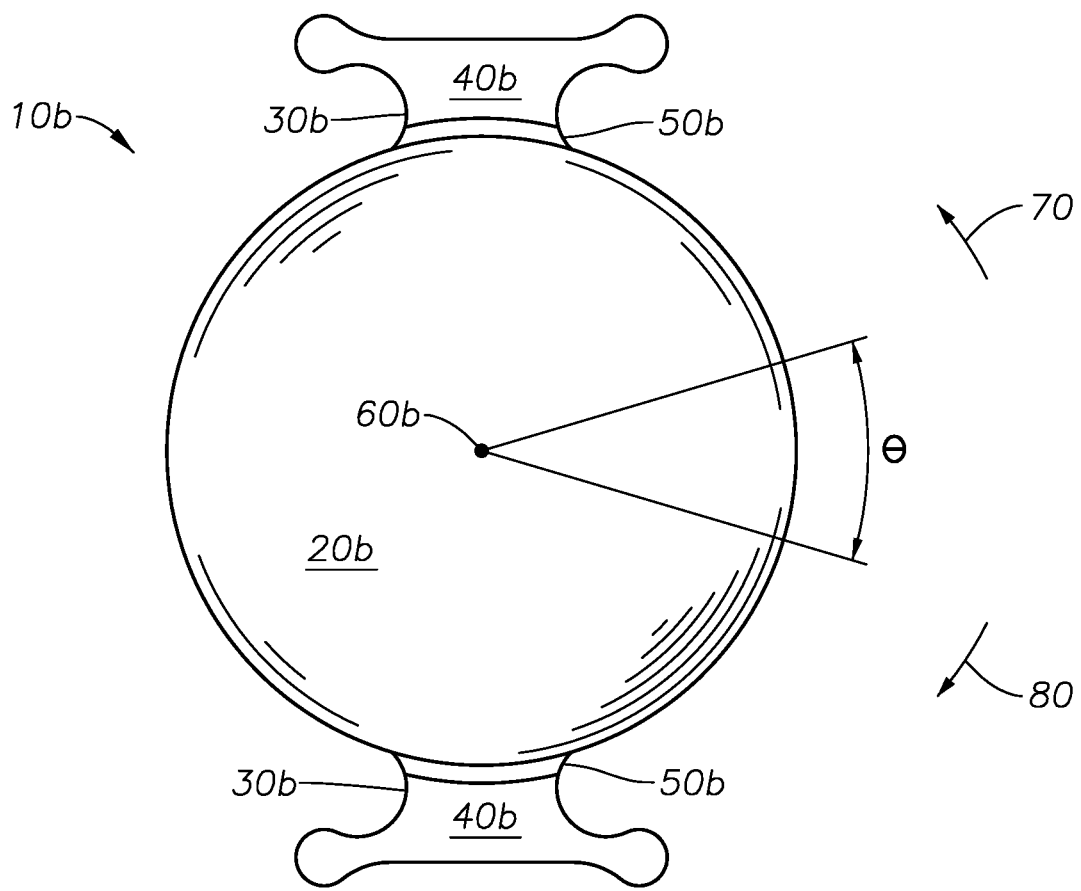
FIG. 2A is a schematic top view diagram of a two-piece IOL.
Figure 2B:
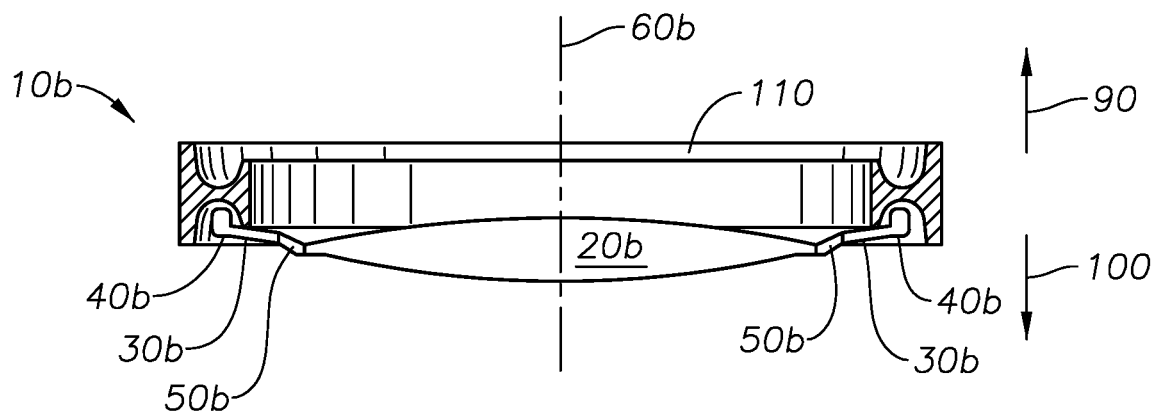
FIG. 2B is a schematic side-view diagram of the two-piece IOL of FIG. 2A.

FIG. 2A is a schematic diagram of an IOL $10b$ including an optic $20b$ and two haptics $30b$ that are attached to the optic $20b$ or base (not shown). Each of the haptics $30b$ has an arm $40b$ and a haptic junction $50b$ between the arm $40b$ and the optic $20b$. After it is implanted and secure in the capsular bag, the optic of IOL $10b$ can be rotated around the center $60b$ in a direction 70 or a direction 80 by an angle θ. Additionally, as shown in FIG. 2B, the optic $20b$ of IOL $10b$ can be adjusted anteriorly or posteriorly in the eye in directions 90 or 100, respectively, by irradiating the haptic junctions $50b$ to cause the PD-LNC to change shape. FIG. 2B also illustrates how the optic $20b$ may be positioned within a base 110, in accordance with some embodiments of a two-piece IOL.

Figure 3:
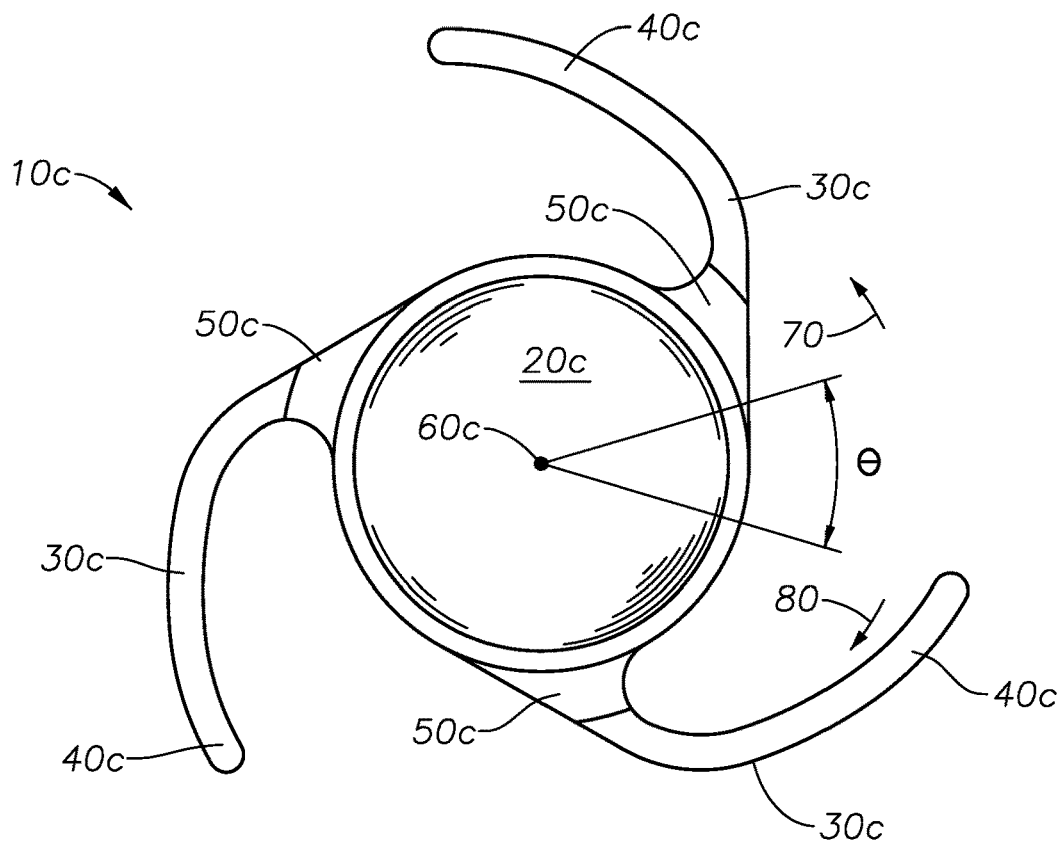
FIG. 3 is a schematic top view diagram of a single-piece IOL having three haptics.

FIG. 3 is a schematic diagram of another IOL $10c$ including an optic $20c$ and three haptics $30c$ attached to the optic $20c$ or base (not shown). Each of the haptics $30c$ has an arm $40c$ and a haptic junction $50c$ between the arm $40c$ and the optic $20c$. The haptic junction $50c$ may attach the haptic $30c$ to the optic $20c$. The IOL also has a center $60c$. After it is implanted and secure in the capsular bag, the optic of IOL $10c$ can be rotated around the center $60c$ in a direction 70 or a direction 80 by an angle θ and/or adjusted posteriorly or anteriorly in the eye by irradiating one or more of the haptic junctions $50c$ to cause the PD-LNC to change shape.

Figure 4:
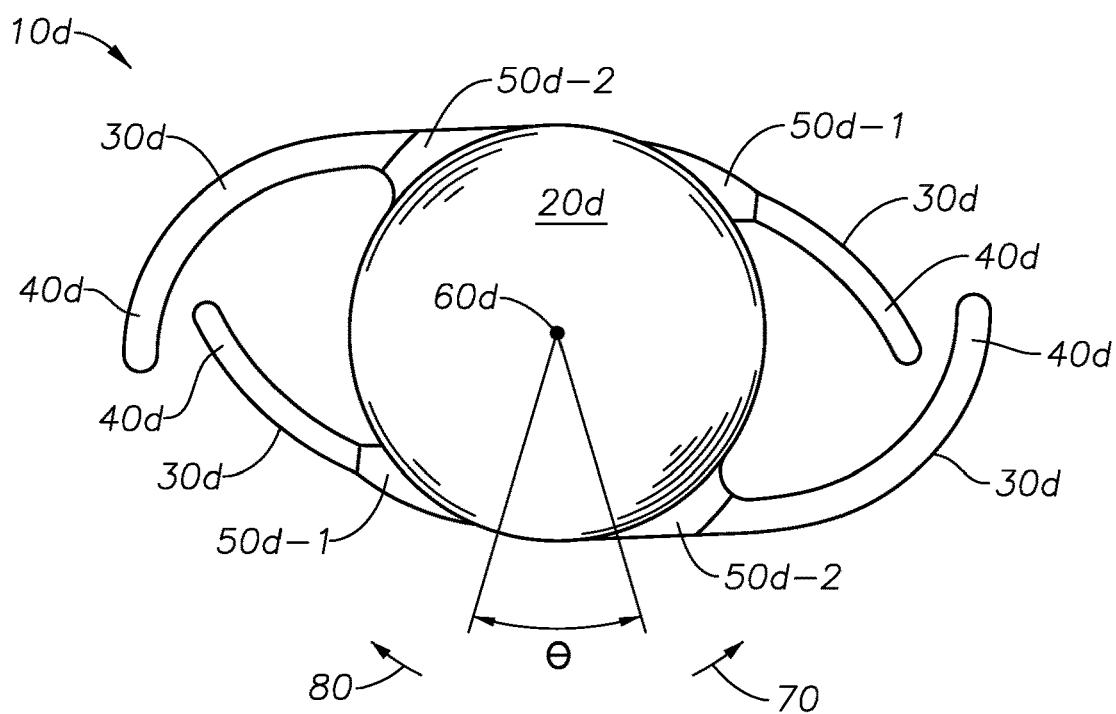
FIG. 4 is a schematic top view diagram of a single-piece IOL having four haptics.

FIG. 4 is a schematic diagram of another IOL $10d$ including an optic $20d$ and four haptics $30d$ attached to the optic $20d$ or a base (not shown). Each of the haptics $30d$ has an arm $40d$ and a haptic junction $50d$-1 or $50d$-2 between the arm $40d$ and the optic $20d$. Each haptic junction $50d$-1 or $50d$-2 may attach the haptic $30d$ to the optic $20d$ or base. The IOL also has a center $60d$. After it is implanted and secure in the capsular bag, the optic of IOL $10d$ can be rotated around the center $60d$ in a direction 70 or a direction 80 by an angle θ and/or adjusted posteriorly or anteriorly in the eye by irradiating one or more of the haptic junctions $50d$-1 and/or $50d$-2 to cause the PD-LNC to change shape. Haptic junctions $50d$-1 may be formed from the same PD-LCN as haptic junctions $50d$-2 or from a different PD-LCN. For example haptic junctions $50d$-1 may have a different wt % of diacrylate azobenzene liquid crystal monomer or a different crosslink density than haptic junctions $50d$-2, allowing the haptic junctions to respond differently to polarized laser radiation.

Figure 5:
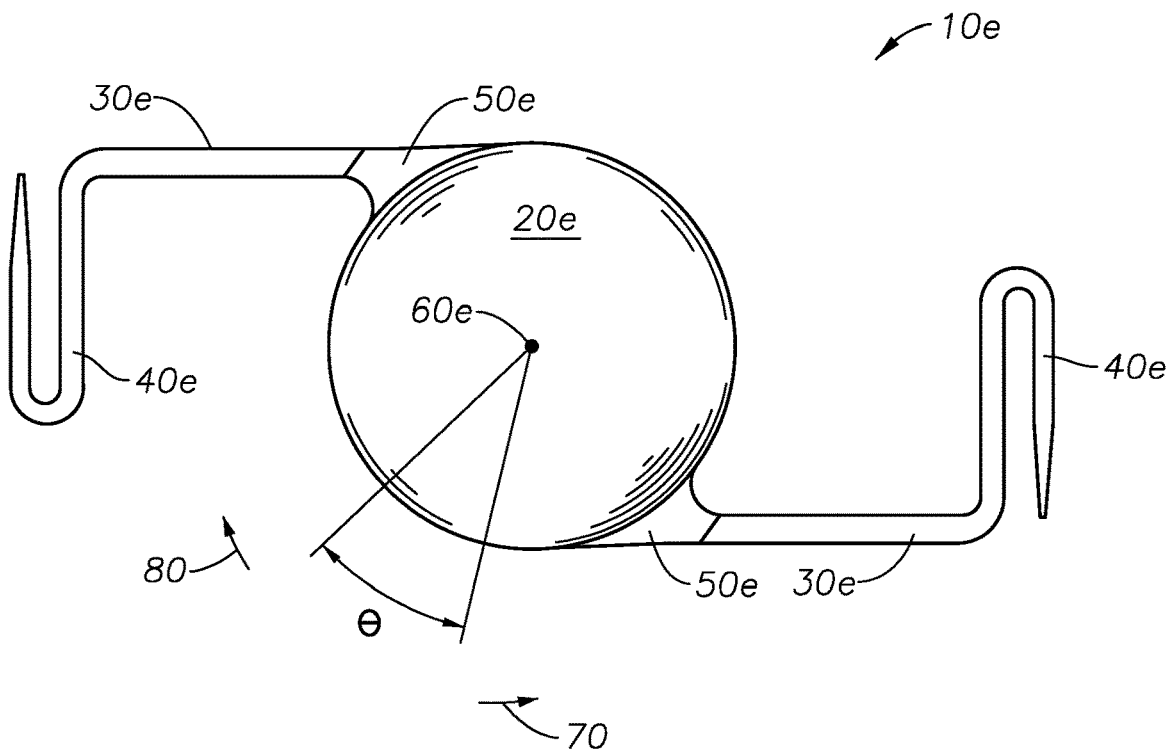
FIG. 5 is a schematic top view diagram of a single-piece IOL having two haptics with a complex structure.

FIG. 5 is a schematic diagram of another IOL $10e$ including an optic $20e$ and two haptics $30e$ attached to the optic $20e$ or base (not shown). Both of the haptics $30e$ has an arm $40e$ and a haptic junction $50e$ between the arm $40e$ and the optic $20e$. The haptic junction $50e$ may attach the haptic $30e$ to the optic $20e$. The IOL also has a center $60e$. After it is implanted and secure in the capsular bag, the optic $20e$ of IOL $10e$ can be rotated around the center $60e$ in a direction 70 or a direction 80 by an angle θ and/or adjusted posteriorly or anteriorly in the eye by irradiating one or more of the haptic junctions $50e$ to cause the PD-LNC to change shape.

Figure 6:
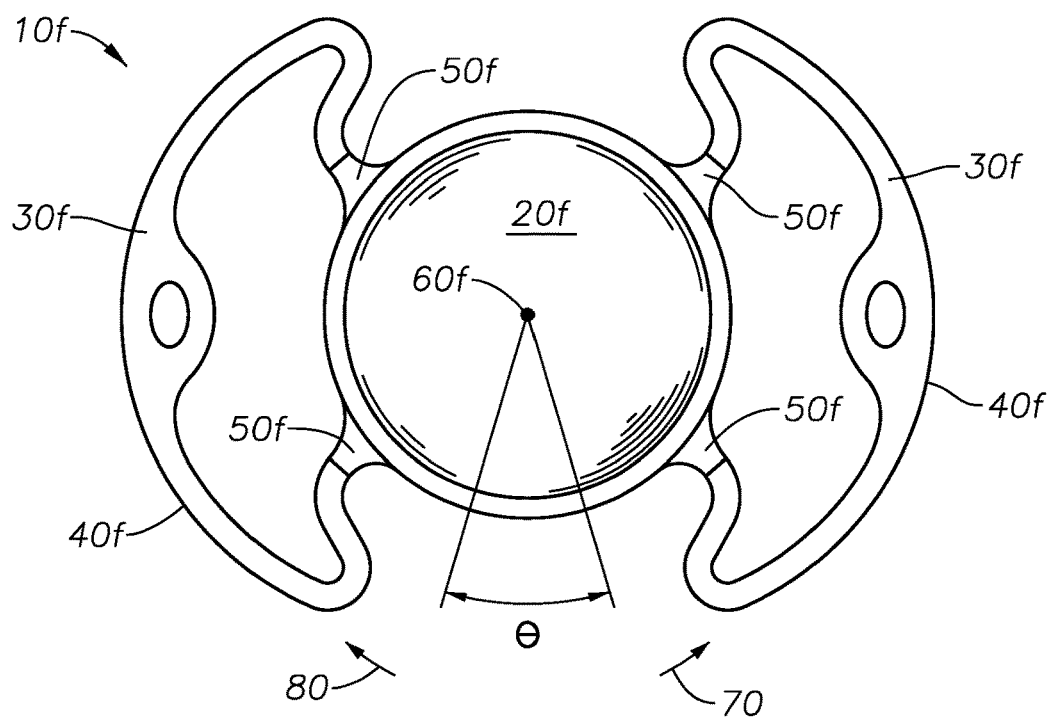
FIG. 6 is a schematic top view diagram of a single-piece IOL having two looped haptics.

FIG. 6 is a schematic diagram of another IOL $10f$ including an optic $20f$ and two looped haptics $30f$ attached to the optic $20f$ or a base (not shown). Each of the haptics $30f$ has an arm $40f$ and at least one haptic junction $50f$ between the arm $40f$ and the optic $20f$. The haptic junction $50f$ may attach the haptics $30f$ to the optic $20f$. The IOL also has a center $60f$. After it is implanted and secure in the capsular bag, the optic $20f$ of IOL $10f$ can be rotated around the center $60f$ in a direction 70 or a direction 80 by an angle θ and/or adjusted posteriorly or anteriorly in the eye by irradiating one or more of the haptic junctions $50f$ to cause the PD-LNC to change shape.

Figure 7:
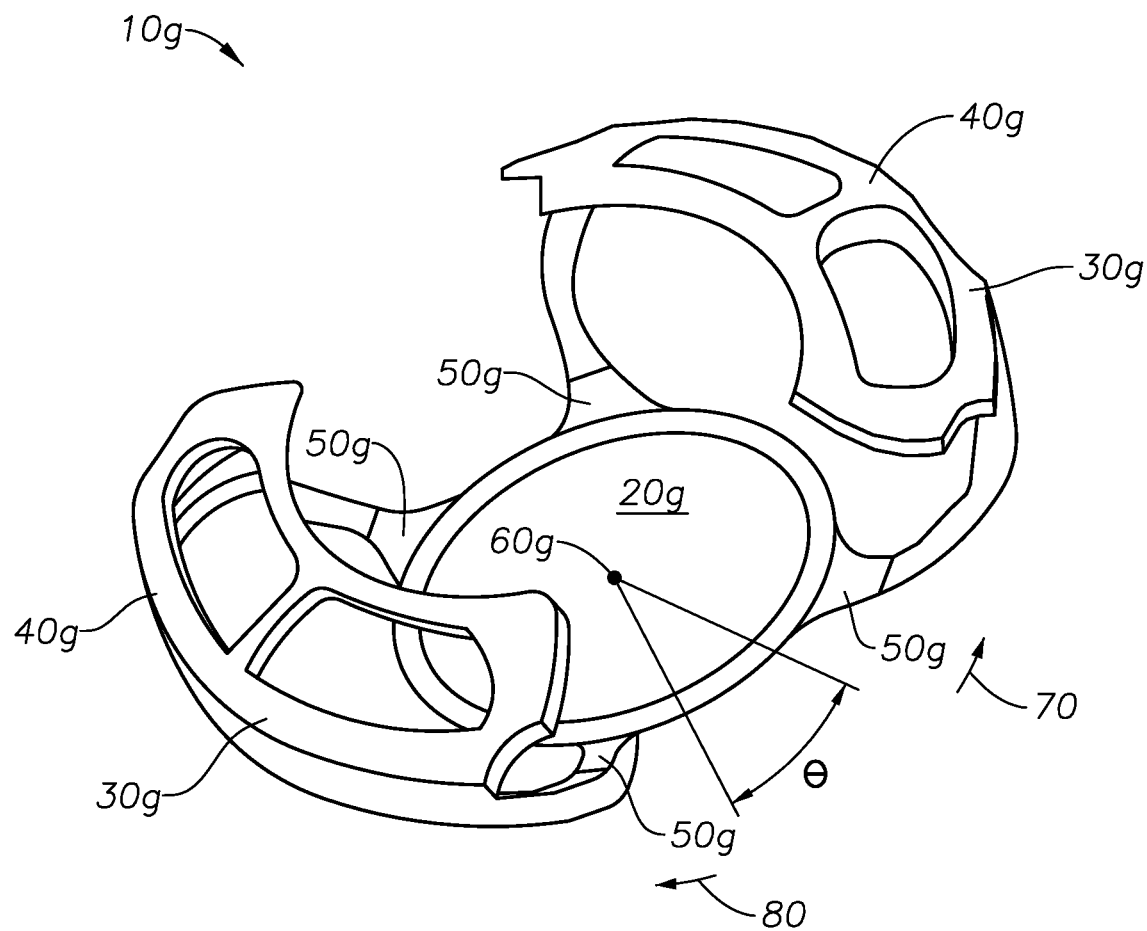
FIG. 7 is a schematic perspective view diagram of a single-piece IOL having two three-dimensional haptics.

FIG. 7 is a schematic diagram of another IOL 10g including an optic 20g and two three-dimensional haptics 30g attached to the optic 20g or a base (not shown). Each of the haptics 30g has an arm 40g, which in this example has a complex three-dimensional structure, and at least one haptic junction 50g between the arm 40g and the optic 20g. The haptic junctions 50g may attach the haptics 30g to the optic 20g. The IOL also has a center 60g. After it is implanted and secure in the capsular bag, the optic of IOL 10g can be rotated around the center 60g in a direction 70 or a direction 80 by an angle θ and/or adjusted posteriorly or anteriorly in the eye by irradiating one or more of the haptic junctions 50g to cause the PD-LNC to change shape.

In FIGS. 1A-7, the entire haptic 30 may be formed from PD-LCN, or only a portion thereof may be formed from PD-LCN. In particular, the haptic junction 50 may be formed from PD-LCN and attached to both the remaining portion of the haptic 30, such as the arm 40, and the optic 20 or the base 110. In addition, the haptic 30 or the haptic junction 50 may be formed from more than one type of PD-LCN. For example, the PD-LCN in different portions of the haptic 30 or the haptic junction 50 may vary in composition or in crosslink density to provide different degrees of responsiveness to polarized laser radiation.

The PD-LCN suitable for use in the present disclosure may be any biocompatible PD-LCN that bends in response to exposure to polarized laser radiation in the range of 440 nm to 514 nm, in the range of 457 nm to 514 nm, or in the range of 440 nm to 445 nm, with the ranges including the endpoints, or particularly 442 nm.

The PD-LCN may include crosslinked diacrylate liquid crystal monomer and diacrylate azobezene liquid crystal monomer. The diacrylate azobenzene liquid crystal mono- 25 wt %, between 5 wt % and 20 wt %, between 5 wt % and 15 wt %, between 5 wt % and 10 wt %, between 10 wt % and 25 wt %, between 10 wt % and 20 wt %, between 10 wt % and 15 wt %, between 15 wt % and 25 wt %, between 15 wt % and 20 wt %, or between 20 wt % and 25 wt %, where ranges between two amounts include the endpoints.

PD-LCNs with lower crosslink density exhibit a more pronounced bending response upon exposure to polarized laser radiation than PD-LCNs with higher crosslink density. For many IOLs, a more pronounced bending response is desired to limit the amount of time it takes to induce the response. However, for IOLs where more controlled bending is useful, PD-LCN crosslink density may be increased. In addition, some degree of crosslinking is needed to form a stable PD-LCN.

The crosslink density may be affected by formation conditions, particularly the length of photocuring the monomers in the presence of one another to induce crosslinking. In addition, the crosslink density may be influenced by the molecular weights of the monomers, with lower molecular weight monomers producing PD-LCN with a higher crosslink density, all other factors being equal.

Typically, the PD-LCN used in the haptic 30 or the haptic junction 50 will have a crosslink density of between 1.0 mol/dm$^3$ and 8.0 mol/dm$^3$.

One suitable diacrylate liquid crystal monomer for use in the present disclosure is 4-(3-Acryloyloxypropyloxy)-benzoesure 2-methyl-1,4-phenylester (also known as 2-Methylbenzene-1,4-diyl bis {4-[3-(acryloyloxy) propoxy] benzoate}), which has the following structural formula:

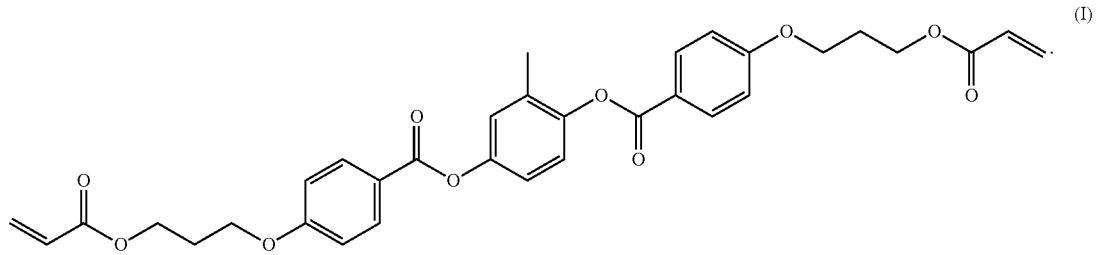 [SMILES: C=CC(=O)OCCCOc1ccc(C(=O)Oc2ccc(OC(=O)c3ccc(OCCCOC(=O)C=C)cc3)c(C)c2)cc1]

mer may be present in an amount of 25 wt % or less, 20 wt % or less, 15 wt %, or less, 10 wt % or less, 5 wt % or less, between 0.1 wt % and 25 wt % between 0.1 wt % and 20 wt %, between 0.1 wt % and 15 wt %, between 0.1 wt % and Suitable diacrylate azobezene liquid crystal monomers for use in the present disclosure include 4,4'-bis[6-acryloloxy) hexyloxy] azobenzene, which has the following structural formula:

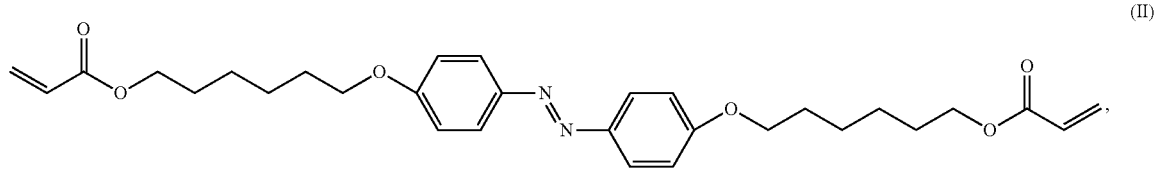 [SMILES: C=CC(=O)OCCCCCCOc1ccc(/N=N/c2ccc(OCCCCCCOC(=O)C=C)cc2)cc1]

10 wt %, between 0.1 wt % and 5 wt %, between 1 wt % and 25 wt %, between 1 wt % and 20 wt %, between 1 wt % and 15 wt %, between 1 wt % and 10 wt %, between 1 wt % and 5 wt %, between 3 wt % and 25 wt %, between 3 wt % and 20 wt %, between 3 wt % and 15 wt %, between 3 wt % and 10 wt %, between 3 wt % and 5 wt %, between 5 wt % and as well as diacrylates of 4-heptyl 4'-propylazobenzene, 4-octyl 4'-propylazobenzene, 4-cyano 4'-heptyloxyazobenzene, and 4-cyano 4'-octyloxyazobenzene.

Although PD-LCN is discussed in detail as an example of a photoresponsive shape memory polymer network, other photoresponsive shape memory polymer networks may be used in the same manner as PD-LCN. For example, a photoresponsive shape memory polymer network with one or more crosslinkers other than a diacrylate or with different monomers may be used. In photoresponsive shape memory polymer network including a PD-LCN, an additive may be used. In general, the photoresponsive shape memory polymer network need only bend in a predictable way, such as at a predictable bending angle, in response to polarized laser radiation, particularly to polarized laser radiation with a given polarization angle.

Figure 8:
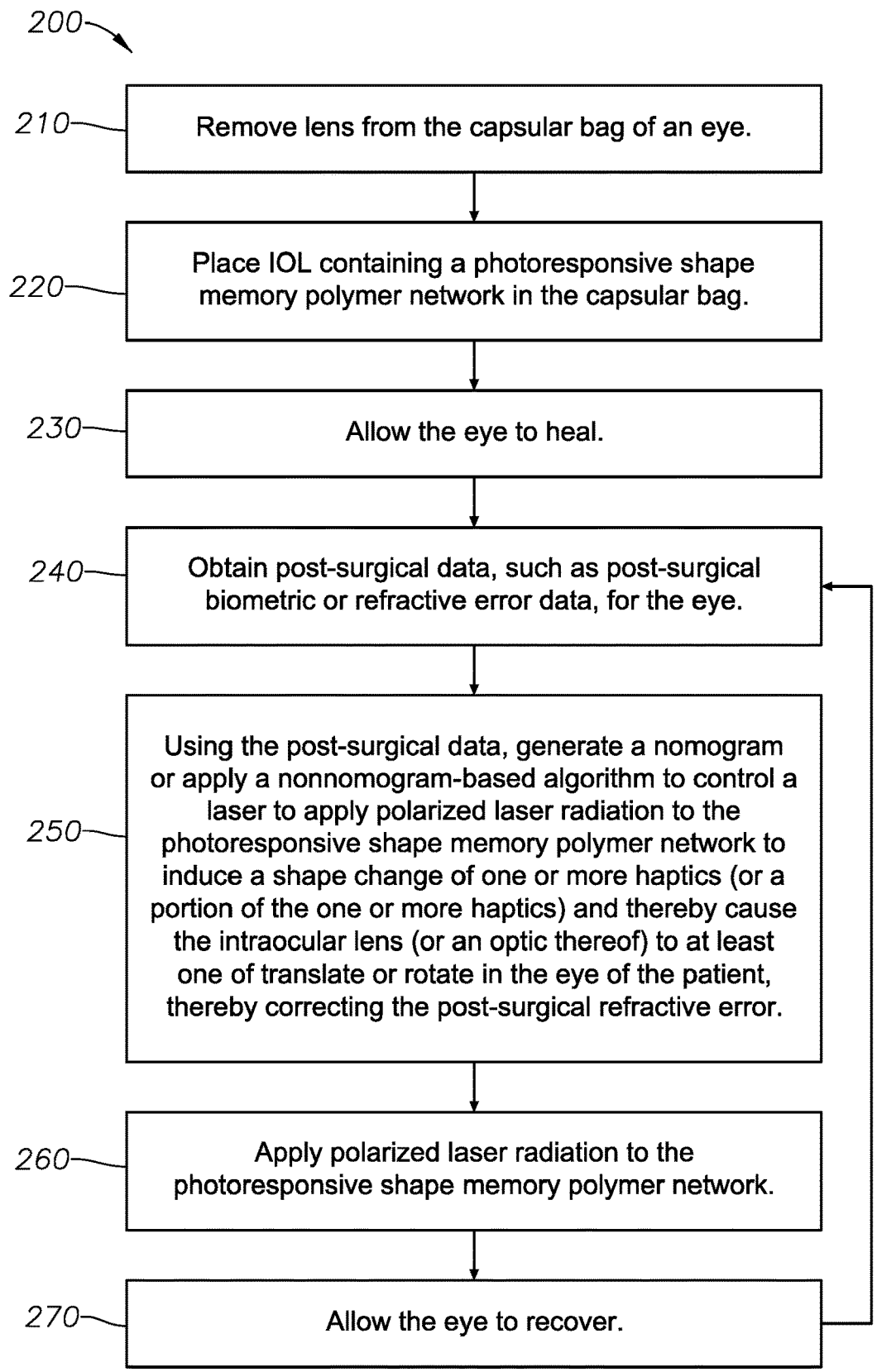
FIG. 8 is a flow chart of a method of implanting and adjusting an IOL.

The present disclosure further provides a method 200 of implanting and adjusting an IOL, such as IOL 10, containing a photoresponsive shape memory polymer network, such as PD-LCN, in an eye of a patient as shown in the flowchart of FIG. 8. In step 210, the lens (which is typically a natural lens, but may be a prior IOL) is removed from the capsular bag. In step 220, the IOL is placed in the capsular bag. During this step, the surgeon attempts to place the IOL in a selected position, but does not always succeed in doing so. In step 230, the eye is allowed to heal for a duration of time, typically two to four weeks. The IOL may move or change position within the eye during this time.

In step 240, the patient undergoes a diagnostic eye exam, typically days, weeks, or months after surgery to obtain post-surgical data. In step 240, biometric data of the eye may be obtained. In step 240, quality of vision data, such a refractive error, including simple refraction measurement or, where appropriate more complex measurements, such as axis of astigmatism, may also be obtained. Step 240 may also be initiated as an IOL maintenance step, often weeks, months, or years after initial IOL placement.

In step 250, based at least in part on information from the diagnostic eye exam, such as post-surgical biometric data and post-surgical refractive error it is determined whether the patient's quality of vision may be improved. For example, the patient may experience sub-optimal refraction in the eye, or may still experience astigmatism. The diagnostic eye exam may, for example measure refraction or cylinder using, for example, a refractometer or an aberrometer.

In step 250, based on data from the diagnostic eye exam, such as post-surgical biometric data and post-surgical refractive error, a nomogram may be generated to control a laser to apply polarized laser radiation to a photoresponsive shape memory polymer network, such as PD-LCN, to induce a shape change of the haptics and thereby cause the intraocular lens to at least one of translate or rotate in the eye of the patient, thereby correcting the post-surgical refractive error. The nomogram may, for example, be used to determine an angle of bending of the photoresponsive shape memory polymer network, such as PD-LCN, and the polarized laser radiation, including the polarization angle, that will achieve the angle of bending. Alternatively, a non-nomogram-based algorithm may be used to control the laser in the same fashion. The nomogram may be generated or the non-nomogram-based algorithm may be executed using a programmed computer, which may also be able to receive and store data from the diagnostic eye exam.

In step 260, polarized laser radiation with a polarization angle and for a time sufficient to cause the portion of the IOL to bend is applied to at least a portion of an IOL haptic containing the photoresponsive shape memory polymer network, such as PD-LCN, adjusting the position of the IOL in the capsular bag.

The portion of the IOL containing the photoresponsive shape memory polymer network, such as PD-LCN, that is irradiated may be the haptic junction, or another part of the haptic that can be reached via polarized laser radiation when the pupil of the eye is dilated. Accordingly, before the portion of the IOL haptic containing the photoresponsive shape memory polymer network, such as PD-LCN, is irradiated with polarized laser radiation, the pupil of the patient's eye may be dilated to allow access to the photoresponsive shape memory polymer network, such as PD-LCN. In methods where the portion of the IOL containing photoresponsive shape memory polymer network, such as PD-LCN, is normally covered by the pupil and not exposed to light, there may not be a need for the patient to wear protective glasses after any surgical procedures to implant or adjust the position of the IOL.

The polarized laser radiation may be provided by any laser able to supply a wavelength able to cause bending of the photoresponsive shape memory polymer network, such as PD-LCN, when passed through a polarization filter. For example, the laser may be a femtosecond or excimer laser. The wavelength may be in the range of 440 nm to 514 nm, in the range of 457 nm to 514 nm, or in the range of 440 nm to 445 nm, with the ranges including the endpoints, or particularly 442 nm.

The polarization filter may be part of the laser, or otherwise placed between the laser and the eye using suitable optics.

Figure 9:
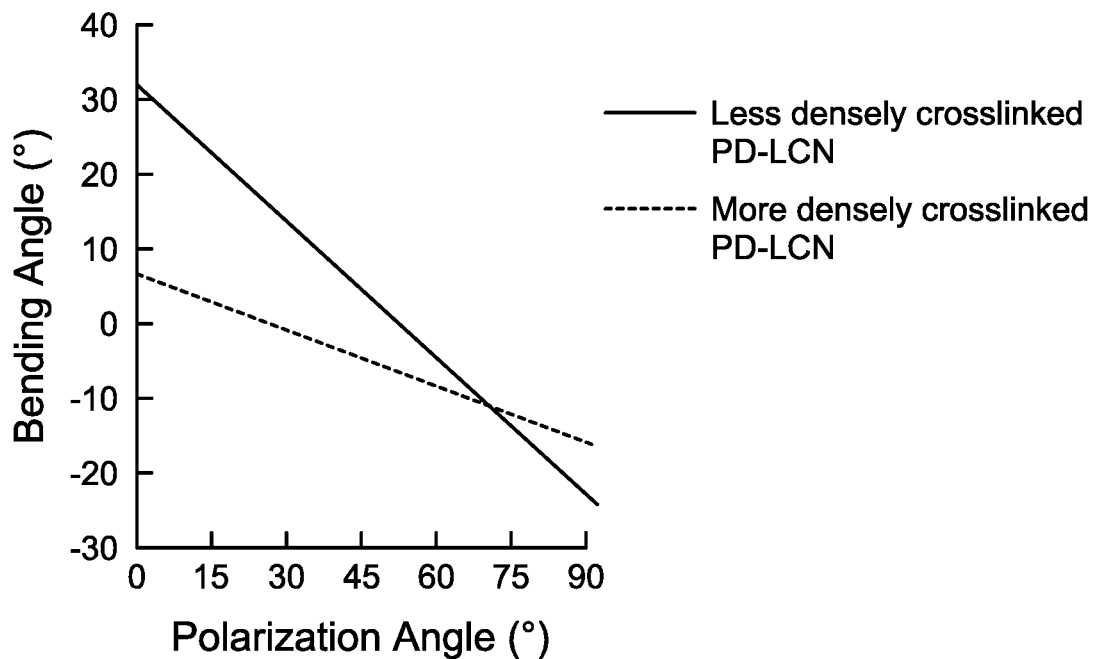
FIG. 9 is an example graph of the relationship between PD-LCN bending angle and polarization angle of laser radiation.

The polarization angle may be selected based on the degree of bending of the photoresponsive shape memory polymer network, such as PD-LCN, to be achieved. As illustrated in FIG. 9, a thin strip of PD-LCN, such as may be contained in the haptic, will bend a predictable angle in response to a particular degree of polarized laser radiation. This bending angle and polarization angle relationship tends to be linear. The responsiveness of the bending angle may be determined, in part, by the crosslink density of the PD-LCN.

Irradiation with the polarized laser continues for an amount of time determined to be appropriate to achieve the target bending angle. For example, the amount of time may be 5 minutes or less, 2 minutes or less, one minute or less, between 0.5 seconds and 1 minute, between 0.5 seconds and 2 minutes, between 0.5 seconds and 5 minutes, between 5 seconds and 1 minute, between 5 seconds and 2 minutes, or between 5 seconds and 5 minutes, where ranges between two amounts include the endpoints. Irradiation may be constant or pulsed.

The same haptic may be irradiated more than once to obtain the correct bending angle. In addition, although only one haptic may be irradiated, for many adjustments, more than one or all haptics will be irradiated.

Depending on the physical shape of the portion of the haptic irradiated, which haptics are irradiated, the position of the haptic(s) in the capsular bag, and the degree of photoresponsive shape memory polymer network, such as PD-LCN, bending induced, the IOL will move to an adjusted position within the capsular bag.

For example, if the haptics of the IOL are subjected to laser radiation at a polarization angle that causes the haptics to push against the posterior region of the capsular bag, the IOL will be moved axially forward in the capsular bag, to a position that is more anterior in the eye. If the haptics of the IOL are subjected to laser radiation at a polarization angle that causes the haptics to push against the anterior region of the capsular bag, the IOL will be moved axially backward in the capsular bag, to a position that is more posterior in the eye. These simple forward and backward axial adjustments may change the diopter of the IOL, and correct refractive errors.

More complex IOLs may bend to push against different portions of the capsular bag, or to internally rotate, allowing rotation of the IOL optic around a center by a target angle. This may be useful, for example, when the patient has astigmatism and the IOL is not properly aligned with the axis of astigmatism.

The location and degree of bending and the polarization angle may be calculated using a computer programmed to access data regarding the eye and the IOL, to calculate the effects of laser irradiation on bending and location of the IOL optic, and to select an appropriate location and duration of laser radiation to achieve the target position of the IOL.

The location and duration of laser radiation and, in some systems, also the placement of the polarization filter and thus the polarization angle may also be implemented using a computer programmed to control the laser. The computer may be the same as the computer programmed to calculate how to achieve the target position of the IOL, or a different computer.

For purposes of this disclosure, a computer includes a processor, memory, and a communications interface.

In step 270, the eye is allowed to recover for a duration of time sufficient to then obtain accurate eye exam results. Typically the pupil is dilated prior to step 260, so the duration of time may be at least long enough for pupil dilation to cease. For example, the duration of time may be at least a day or at least a week.

The process then returns to step 240 and the patient is again evaluated to determine if the actual IOL position is the target position.

Although method 200 is described with multiple steps, the disclosure includes other methods encompassing only a portion of those steps, such as steps 240 through 260, or steps 250 through 270.

After bending, the photoresponsive shape memory polymer network, such as PD-LCN, remains in position indefinitely, making adjustments using method 200 permanent unless the IOL shifts due to other causes. However, the photoresponsive shape memory polymer network, such as PD-LCN, can readily be bent multiple times to different degrees by irradiating the photoresponsive shape memory polymer network, such as PD-LCN, with laser radiation having a different polarization angle. So, for example, if the IOL optic is moved too far forward in the eye in step 260, the same haptic may be irradiated with laser radiation at a different polarization angle, causing it to bend to a lesser degree, effectively moving the IOL optic backwards in the eye.

Figure 10:
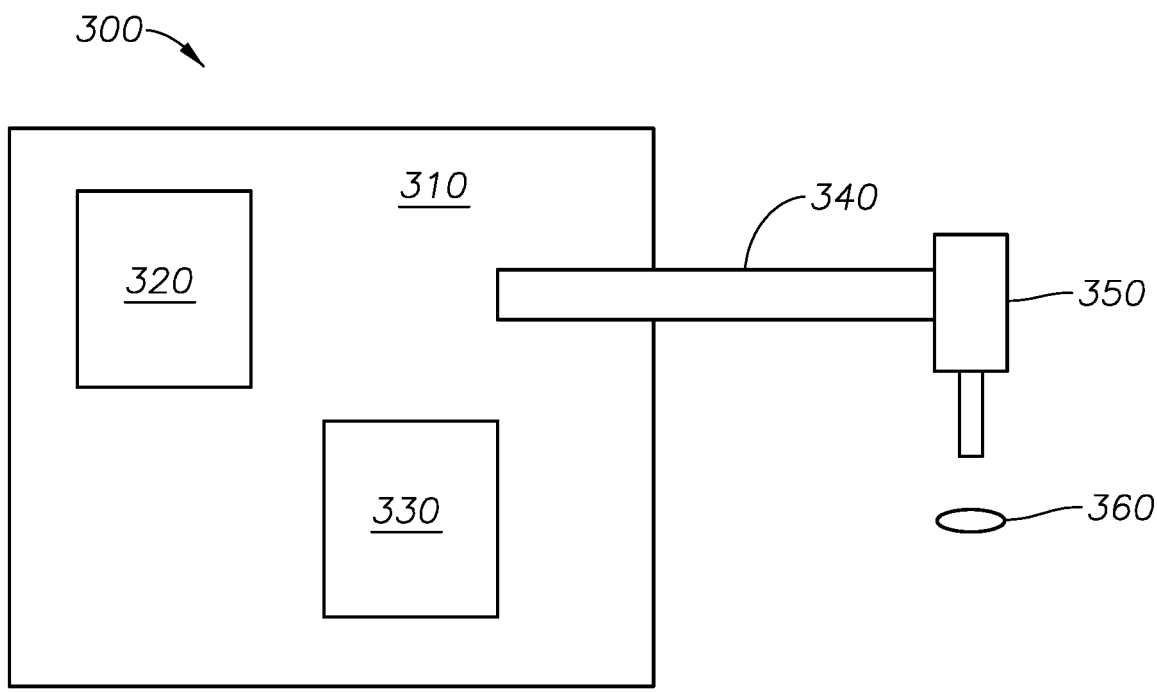
FIG. 10 is a diagram of a surgical system for adjusting the position of an IOL.

The present disclosure further includes a surgical system 300, as illustrated in FIG. 10, for adjusting the position of an IOL, such as an IOL 10, in the capsular bag of an eye. The system 300 includes a computer 310, which includes a processor 320, a memory 330, and a communications interface 340. The system 300 also includes a laser 350 which is able to provide laser radiation in a suitable range to induce shape change in the haptic material, such as in the range of 440 nm to 514 nm, in the range of 457 nm to 514 nm, or in the range of 440 nm to 445 nm, with the ranges including the endpoints, or particularly 442 nm. System 300 may further include a polarization filter 360, which is able to adjust the polarization angle of radiation from the laser 350. The polarization filter 360 may be part of the laser 350, or a separate component.

The computer 310 may include in the memory 330 instructions that, when executed by the processor 320, cause instructions to be sent through the communications interface 340 to cause the laser 350 and the polarization filter 360 to irradiate certain portions of the IOL, in the capsular bag of a patient's eye, to cause the photoresponsive shape memory polymer network, such as PD-LCN, of the IOL to bend. In particular, when the instructions are executed by the processor 320, they may cause the laser 350 and the polarization filter 360 to implement step 260 of method 200. Additionally, memory 330 may store instructions for generating, based on patient-specific biometric, wavefront, and/or other measurements taken post-surgery, an algorithm or nomogram to cause laser 350 to apply light to the haptics so as to induce a shape change which will cause the lens to change position and thereby correct any residual refractive error and/or toric misalignment.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

The invention claimed is:

1. An in-situ adjustable ophthalmic device, comprising:
a ring-shaped intraocular base comprising an opening configured to receive an optic of an intraocular lens (IOL); and
an intraocular lens (IOL) comprising an optic and at least two haptics, each haptic coupled to the optic via a haptic junction, the at least two haptics configured to engage with the intraocular base,
wherein each of the haptic junctions comprises a photoresponsive shape memory polymer network,
wherein the intraocular base and IOL are configured to be positioned in a capsular bag of a patient, and further configured such that irradiation of the haptic junctions with polarized laser radiation induces a shape change of the photoresponsive shape memory polymer network, and therefore a shape change of the haptics, to cause the IOL to be rotated around a center of the optic, with respect to the intraocular base, in a clockwise direction or counterclockwise direction,
wherein a first haptic junction of the haptic junctions comprises the photoresponsive shape memory polymer network in a first placement, and a second haptic junction of the haptic junctions comprises the photoresponsive shape memory polymer network in a second placement different from the first placement, such that the at least two haptics are configured to respond differently to irradiation.

2. The adjustable ophthalmic device of claim 1, wherein the photoresponsive shape memory polymer network comprises a polydomain azo liquid crystalline polymer network (PD-LCN).

3. The adjustable ophthalmic device of claim 2, wherein the PD-LCN comprises crosslinked diacrylate azobenzene liquid crystal monomer.

4. The adjustable ophthalmic device of claim 2, wherein the polarized laser radiation has a wavelength in the range of 440 nm to 514 nm.

* * * * *